United States Patent
Rondot et al.

(10) Patent No.: US 6,979,754 B2
(45) Date of Patent: Dec. 27, 2005

(54) METHOD FOR OBTAINING POLYMERIZABLE VINYL CHLORIDE FROM A RAW PRODUCT DERIVED FROM THE PYROLYSIS OF 1,2-DICHLOROETHANE

(75) Inventors: Béatrice Rondot, Beauvoisin (FR); François Vanney, Lyons (FR)

(73) Assignee: ARKEMA, Puteaux (FR)

( * ) Notice: Subject to any disclaimer, the term of this patent is extended or adjusted under 35 U.S.C. 154(b) by 0 days.

(21) Appl. No.: 10/492,976

(22) PCT Filed: Oct. 15, 2002

(86) PCT No.: PCT/FR02/03518

§ 371 (c)(1),
(2), (4) Date: Aug. 19, 2004

(87) PCT Pub. No.: WO03/033443

PCT Pub. Date: Apr. 24, 2003

(65) Prior Publication Data

US 2004/0267064 A1 Dec. 30, 2004

(30) Foreign Application Priority Data

Oct. 17, 2001 (FR) .................................. 01 13364

(51) Int. Cl.$^7$ ............................................. C07C 17/38
(52) U.S. Cl. .................... 570/238; 422/288; 570/220
(58) Field of Search ............................... 570/220, 238; 422/288

(56) References Cited

U.S. PATENT DOCUMENTS

| 3,125,607 | A | | 3/1964 | Keating, et al. |
| 3,125,608 | A | | 3/1964 | McDonald |
| 3,142,709 | A | | 7/1964 | Gause, et al. |
| 3,801,660 | A | | 4/1974 | Coppens |
| 3,867,263 | A | * | 2/1975 | Wall, Jr. ...................... 203/81 |
| 3,876,714 | A | * | 4/1975 | Coppens .................... 570/238 |
| 4,760,206 | A | * | 7/1988 | Schneider .................. 570/220 |
| 6,160,189 | A | * | 12/2000 | Olinger et al. ............. 570/238 |

FOREIGN PATENT DOCUMENTS

| EP | 0 073 941 | 3/1983 |
| FR | 1 216 030 | 4/1960 |
| FR | 1 602 522 | 1/1971 |
| GB | 1 218 224 | 1/1971 |

* cited by examiner

Primary Examiner—Michael L. Shippen
(74) Attorney, Agent, or Firm—Smith, Gambrell & Russell, LLP

(57) ABSTRACT

The invention concerns a method for obtaining directly polymerisable vinyl chloride which consists in subjecting a cooled raw product derived from of pyrolysis of 1,2-dichloroethane, to another cooling process at a temperature not more than 40° C., under pressure ranging between 10 to 15 bars then in leaving it at substantially identical temperature and pressure levels for a duration not more than 20 minutes. The invention also concerns a device for implementing the method.

13 Claims, 1 Drawing Sheet

METHOD FOR OBTAINING POLYMERIZABLE VINYL CHLORIDE FROM A RAW PRODUCT DERIVED FROM THE PYROLYSIS OF 1,2-DICHLOROETHANE

FIELD OF THE INVENTION

The invention relates to a method for obtaining vinyl chloride capable of polymerization, from a raw product derived from the pyrolysis of 1,2-dichloroethane.

The invention also relates to an apparatus for implementing the method.

BACKGROUND OF THE INVENTION

The products obtained from pyrolyzing 1,2-dichloroethane, hereafter denoted by DCE, contain in particular small quantities of 1,3-butadiene, of the order of 10 to 100 parts per million (ppm), relative to vinyl chloride. These contents of 1,3-butadiene, denoted hereafter by BD, which are found in the final vinyl chloride are sufficient to inhibit its polymerization and it is necessary to reduce the BD contents to less than 8 ppm in order to make the vinyl chloride polymerizable under industrial conditions.

It has often been found that the content of BD formed during pyrolysis of DCE is lower the purer said DCE used, but it is always necessary to limit the BD content in the vinyl chloride obtained by pyrolysis of DCE in order for vinyl chloride polymerization to be able to proceed normally.

To do this, many methods have been proposed. In the majority of cases, these methods involve, in order to remove the BD, chlorination, hydrochlorination or hydrogenation reactions with or without the presence of catalysts.

Thus, patent FR 1 216 030 proposes to purify the vinyl chloride obtained by pyrolysis of DCE by making the vinyl chloride pass as a mixture with hydrochloric acid, in the vapor phase, over a hydrochlorination catalyst such as $HgCl_2$ or $FeCl_3$. However, this method requires the inclusion of an additional catalytic treatment plant, thereby possibly considerably increasing the production costs, and requires least some of the unconverted DCE to be separated from the pyrolysis products.

In U.S. Pat. No. 3,125,607, anhydrous chlorine is added to the vinyl chloride at a temperature between. $-20°$ C. and $0°$ C. in a ratio of chlorine to BD to be removed of about 5/1. The BD content passes from 200 ppm to almost 0 ppm after 30 minutes of chlorination.

However, this method has the drawback of including an additional distillation for removing the chlorinated products from the BD, the excess chlorine and various impurities liable to be formed during BD chlorination.

U.S. Pat. No. 3,125,608 discloses a method of purifying gaseous vinyl chloride containing BD, by heating said vinyl chloride with hydrogen to a temperature ranging from $60°$ C. to $250°$ C. in the presence of a catalyst consisting of Pd supported by activated alumina.

This method has the drawback of including an additional hydrogenation plant.

According to the method described in U.S. Pat. No. 3,142,709, the vinyl chloride is purified of BD by bringing liquid vinyl chloride into contact with an amount of anhydrous hydrochloric acid representing from 0.5 to 5% by weight of the vinyl chloride for a period ranging from 2 minutes to 5 hours. However, this method applies only to the vinyl chloride already separated from the other pyrolysis products and involves an additional distillation.

Patent FR 1 602 522 discloses a method for obtaining vinyl chloride immediately capable of polymerization, which consists, starting from the raw product derived from the pyrolysis of DCE, in condensing, under a pressure greater than atmospheric pressure, said raw product in order to obtain a liquid phase that is left to mature for at least two hours at a temperature between $0°$ C. and $100°$ C. before separating the constituents thereof.

According to that method, the liquid phase after such a treatment contains practically no BD. In practice, this liquid phase remains in tanks.

This method applies most particularly to pyrolysis products containing at most 10 ppm BD relative to vinyl chloride.

When the pyrolysis products contain larger amounts of BD, such as for example at most 20 ppm, the process is carried out in the following manner.

After the prior condensation step, which is carried out by suitably cooling the gaseous pyrolysis products maintained at a pressure above atmospheric pressure, a gas phase is obtained which is in equilibrium with the liquid phase and contains a certain amount of BD. The matured liquid phase is used as liquid for scrubbing said gas phase, so as to absorb the residual BD. It then undergoes further maturing for at least two hours. Thus, by repeating this operation, in one or more columns, depending on the BD content in the raw pyrolysis product, it is possible to completely purify vinyl chloride of BD.

Although giving satisfactory results, these various methods of operation have many drawbacks.

For low BD contents, this method applies only to the liquid phase obtained after condensation of the raw product derived from the pyrolysis of DCE and does not take account of the BD contents of the gas phase that may fluctuate and consequently be found in the final vinyl chloride.

When the amounts of BD are higher, at least one operation of scrubbing the gas phase with the liquid phase matured for at least two hours is carried out, which liquid scrubbing phase is again matured for at least two hours.

This process involves many additional items of equipment and the long residence times result in large volumes of inflammable and toxic products under pressure.

DESCRIPTION OF INVENTION

It has found that it is possible to obtain a vinyl chloride capable of polymerization without the drawbacks of the aforementioned methods, by using simple and effective means for reducing the 1, 3-butadiene (BD) content of the entire stream coming form the pyrolysis of DCE.

The subject of the invention is therefore a method for obtaining vinyl chloride immediately capable of polymerization from all of the raw product derived from the pyrolysis of DCE having undergone a cooling operation, said method being characterized in that all of the cooled raw product, consisting of a liquid phase and a gas phase, is cooled further down to a temperature of at most $40°$ C. under a pressure ranging from 10 to 15 bar, and then recovered from a tank at substantially identical temperatures and pressures, in which tank the liquid phase remains for a time of at most 20 minutes, and preferably for a time ranging from 5 to 15 minutes, before separation of the constituents.

According to the present invention, the expression "vinyl chloride capable of polymerization" denotes a vinyl chloride having a BD weight content of at most 8 ppm and preferably between 2 and 7 ppm.

According to the present invention, the gas stream coming from the pyrolysis furnace(s) undergoes suitable cooling, which consists of a succession of quenching and condensation operations, which results in a mixture in which the gas phase is in equilibrium with the liquid phase. This mixture—the cooled raw product—comprises vinyl chloride, hydrogen chloride, unconverted DCE, BD and various byproducts. The amounts of BD may vary widely and depend in particular on the purity of the DCE used and on the conditions under which said DCE is pyrolyzed. They are generally between 10 ppm and 100 ppm in current methods.

According to the present invention, all of the cooled raw product is subjected to a further cooling operation under a pressure of greater than atmospheric pressure in a heat exchanger of the falling-film exchanger type from which it leaves at a temperature of at most 40° C. The pressure within said exchanger is at most 15 bar, and preferably between 10 and 15 bar.

All of the cooled raw product thus treated is immediately collected in a tank under pressure and temperature conditions almost identical to those under which it was cooled in the falling-film exchanger, in which tank the liquid phase remains for a time of at most 20 minutes and preferably for a time ranging from 5 to 15 minutes.

Next, the constituents of the mixture are separated using means known per se. According to the present invention, it is preferred however to separate the hydrogen chloride from the DCE/vinyl chloride mixture in a first distillation column, then the vinyl chloride from the DCE in a second column and, finally, the last traces of HCl are removed in a suitable apparatus.

The vinyl chloride coming from the third column advantageously has a BD content of less than 8 ppm and is then immediately capable of polymerization.

BRIEF DESCRIPTION OF DRAWING

The sole non-limiting FIGURE in this application depicts a schematic of the apparatus of the present invention.

The invention also relates to an apparatus for implementing the method.

Figure 1:
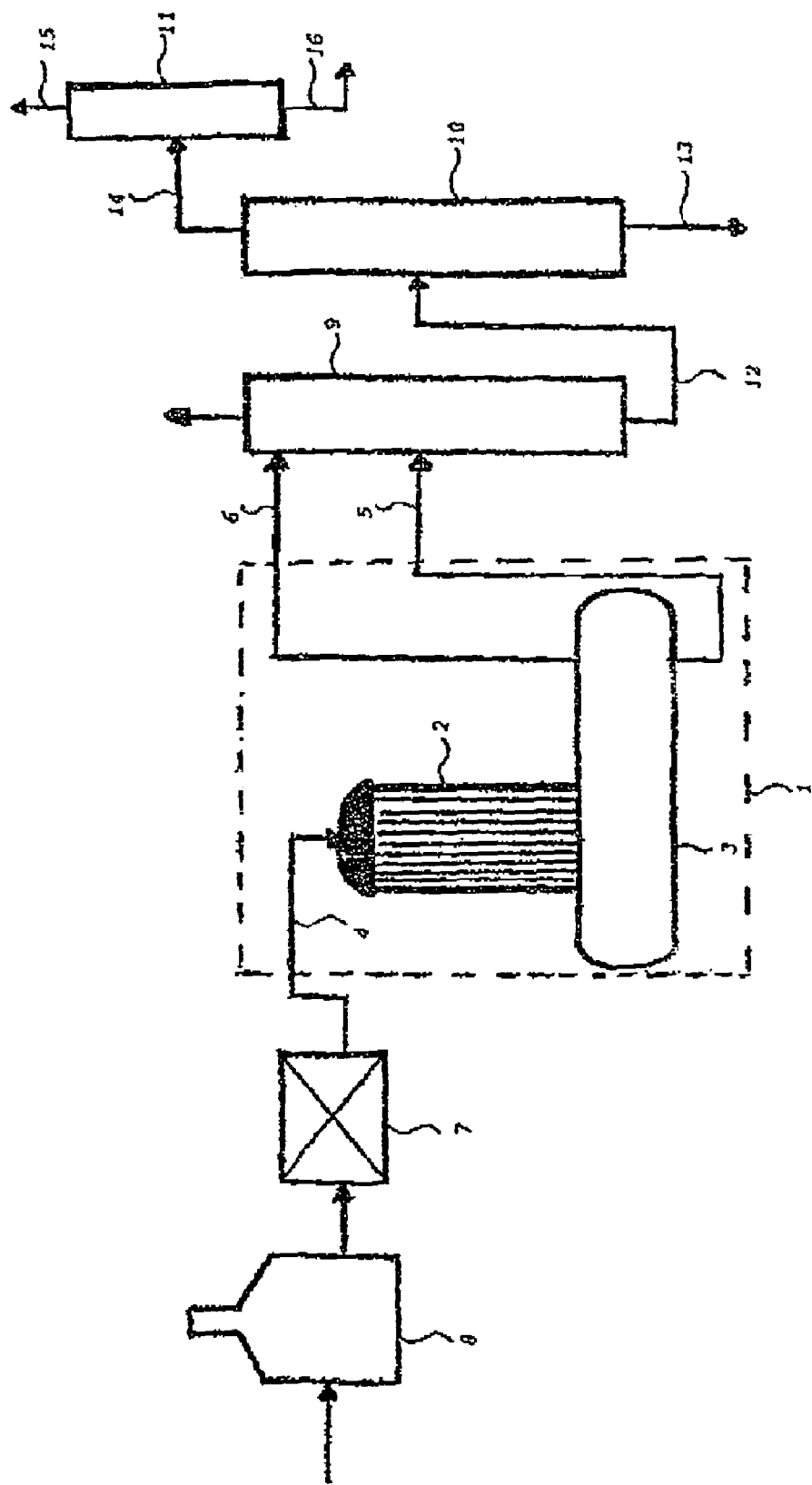

This apparatus (1), placed in a vinyl chloride production plant as shown schematically in FIG. 1 (the dotted area), inserted between a cooling zone (7), for cooling the gas stream (GS) coming from the pyrolysis zone (8), and the HCl distillation column (9), consists of a falling-film heat exchanger (2) placed on top of a receiving pot (3), this being a horizontal cylindrical tank. The exchanger (2) is fed with the entire cooled raw product (at 7) via a line (4). The HCl distillation column is fed with raw product treated in the apparatus (1) with, on the one hand, liquid product via the line (5) and, on the other hand, gaseous product via the line (6). Withdrawn from the column (9) as tops product is HCl and as bottoms product a mixture comprising vinyl chloride, unconverted DCE and various byproducts, which mixture feeds the vinyl chloride distillation column (10) via a line (12), from which column is withdrawn, as tops product, vinyl chloride (14) that is purified in a suitable apparatus (11), from which apparatus it is withdrawn at (16) and that is capable of industrial polymerization.

The unconverted DCE and various byproducts are removed at (13).

The residual HCl is withdrawn at (15).

The apparatus according to the invention is designed in such a way that the exchanger is placed on the receiving pot in such a way that the products from the exchanger flow directly into said pot.

The falling-film exchanger consists of vertical tubes enclosed in a calender, through which tubes the liquid and gas streams flow, the liquid trickling down the walls of said tubes. Cooling is provided by cooling water flowing on the calender side. A person skilled in the art will determine the necessary number of tubes suitable for the streams to be treated and for the cooling.

The method and the apparatus for implementing the method according to the invention allow the BD content in vinyl chloride to be lowered, making it immediately polymerizable. They also have the advantage of relieving the refrigeration demand at the top of the HCl distillation column. The example that follows illustrates the invention.

EXAMPLE

The example is carried out in an industrial plant as shown schematically in FIG. 1 and designed in such a way that it can produce 50 metric tons of immediately polymerizable vinyl chloride per hour.

The pyrolysis zone (8), consisting of three furnaces, is fed with DCE having a purity of 99.7%.

This zone is maintained at a mean temperature of about 480° C. and at a pressure of 30 bar.

The stream coming from this pyrolysis zone, which comprises vinyl chloride (VC), HCl, unconverted DCE (about 50%), BD and other byproducts, leaves at a temperature close to 480° C. and at a pressure of 30 bar and passes into a cooling zone (7), consisting of quenching columns, which lowers its temperature to around 180° C. and into various exchangers with various cold levels, which lower its temperature from 180° C. to about 60° C.

All of the raw product thus cooled that leaves (7), consisting of a gas phase comprising vinyl chloride, HCl, and small amounts of DCE, and of a liquid phase, comprising DCE, vinyl chloride and small amounts of HCl, is introduced into the top of the falling-film exchanger (2) at a temperature of about 56° C. This exchanger consists of 1652 tubes and is cooled with 28° C. water flowing countercurrently through the calender. The pressure inside the falling-film exchanger (2) is 14 bar.

The stream leaves (2) at a temperature of 37° C. and a pressure of 14 bar and falls directly into the pot (3), which is a simple horizontal cylindrical tank, in which the liquid phase remains for 15 minutes at approximately 37° C. and a pressure of 14 bar. The gas and liquid streams are then directed to the distillation column (9) via the lines (6) and (5) respectively. In this column, HCl is separated at the top at about 25° C. and a pressure of 13 bar.

The liquid phase, comprising VC, DCE and various byproducts is withdrawn from the boiler maintained at about 110° C. and sent into the distillation column (10) via the line (12).

In this column, the VC is separated at the top at 30° C. and a pressure of 4 bar.

The bottom of the column (10) maintained at 150° C., essentially contains DCE and various byproducts that are withdrawn at (13). The VC is then sent via the line (14) into the column (11) where the residual HCl is removed, said HCl being withdrawn as top product (15). The VC withdrawn from this column at (16) has a mean BD weight content ranging from 3 to 6 ppm and, as a consequence, is immediately polymerizable on an industrial scale.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The foregoing references are hereby incorporated by reference.

What is claimed is:

1. A method for obtaining vinyl chloride capable of polymerization and formed from all of a cooled raw product derived from pyrolysis of 1,2-dichloroethane and having undergone a cooling operation, comprising:
   (1) providing said cooled raw product, wherein said cooled raw product comprises a mixture of a gas phase and a liquid phase, the gas phase and the liquid phase being in equilibrium with each other, the mixture comprising vinyl chloride, hydrogen chloride, unconverted 1,2-dichloroethane and 1,3-butadiene;
   (2) conveying all of said cooled raw product to a falling-film type heat exchanger and subjecting said cooled raw product to a further cooling operation under a pressure greater than atmospheric pressure to at most 15 bar and a temperature of at most 40° C.;
   (3) conveying all of said further cooled raw product from the falling-film type heat exchanger to a receiving pot, wherein the pot has a temperature and a pressure that are substantially identical to the temperature and the pressure, respectively, in the falling-film type heat exchanger, wherein the liquid phase of the further cooled raw product is permitted to remain in the pot for a period of at most 20 minutes;
   (4) conveying the further cooled raw product to a first distillation column and subjecting the further cooled raw product to a first distillation process to separate hydrogen chloride from the further cooled raw product, thereby forming a first distillation product comprising vinyl chloride and unconverted 1,2-dichloroethane;
   (5) conveying the first distillation product to a second distillation column and subjecting the first distillation product to a second distillation process to separate vinyl chloride from the first distillation product; and
   (6) conveying the separated vinyl chloride to a purification apparatus and subjecting the separated vinyl chloride to a purification process to remove residual hydrogen chloride therefrom, thereby forming a purified vinyl chloride capable of polymerization.

2. The method as claimed in claim 1, wherein the liquid phase remains in the tank for a time ranging from 5 to 15 minutes.

3. The method as claimed in claim 1, wherein said first and second distillation processes are conducted under pressures greater than atmospheric pressure.

4. The method as claimed in claim 1, wherein the purified vinyl chloride has a mean 1,3-butadiene content of from 3 to 6 ppm.

5. The method as claimed in claim 1, wherein in step (4), the hydrogen chloride is removed from a top of the first distillation column and the first distillation product is formed at a bottom of the first distillation column; further wherein in step (5), vinyl chloride is removed from a top of the second distillation column; and further wherein in step (6), the purified vinyl chloride is removed from a bottom of the purification apparatus.

6. The method as claimed in claim 1, wherein the cooled raw product provided in step (1) has a 1,3-butadiene content of from 10 ppm to 100 ppm.

7. The method as claimed in claim 1, wherein the cooled raw product provided in step (1) is derived from pyrolysis of a 1,2-dichloroethane having a purity of 99.7%.

8. The method as claimed in claim 1, wherein the cooled raw product provided in step (1) has a temperature of about 60° C.

9. The method as claimed in claim 1, wherein in step (2), the further cooling operation is conducted under a pressure of from 10 to 15 bar.

10. An apparatus for carrying out a method for obtaining vinyl chloride capable of polymerization and formed from all of a cooled raw product derived from pyrolysis of 1,2-dichloroethane and having undergone a cooling operation, the apparatus comprising:
   (a) a falling-film type heat exchanger adapted to receive said cooled raw product and to further cool the cooled raw product under a pressure of greater than atmospheric pressure to at most 15 bar and a temperature of at most 40° C.;
   (b) a receiving pot adapted to receive the further cooled raw product and to maintain the further cooled raw product at a temperature and a pressure that are substantially identical to the temperature and the pressure under which the cooled raw product was further cooled in the falling-film heat exchanger;
   (c) a first distillation column adapted to receive the further cooled raw product from the receiving pot and to separate hydrogen chloride from the further cooled raw product, thereby forming a first distillation product;
   (d) a second distillation column adapted to receive the first distillation product from the first distillation column and to separate vinyl chloride from the first distillation product; and
   (e) a purification apparatus adapted to receive the separated vinyl chloride from the second distillation column and to remove residual hydrogen chloride from the separated vinyl chloride to purify the vinyl chloride.

11. The apparatus as claimed in claim 10, wherein the falling-film type heat exchanger comprises vertical tubes enclosed in a calender, the tubes being adapted for flow therethrough of the cooled raw product, and the heat exchanger being adapted to allow water to flow countercurrently through the calender.

12. The apparatus as claimed in claim 10, wherein the falling-film type heat exchanger is disposed on top of the receiving pot such that the further cooled raw product flows directly into said pot.

13. The apparatus as claimed in claim 10, wherein the receiving pot is a horizontal cylindrical tank.

* * * * *